United States Patent [19]
Ayer

[11] Patent Number: 5,240,713
[45] Date of Patent: Aug. 31, 1993

[54] DUAL RATE AGENT DELIVERY DEVICE

[75] Inventor: Atul D. Ayer, Palo Alto, Calif.

[73] Assignee: Alza Corporation, Palo Alto, Calif.

[21] Appl. No.: 767,308

[22] Filed: Sep. 27, 1991

[51] Int. Cl.$^5$ ............................................. A61K 9/24
[52] U.S. Cl. .................................. 424/473; 424/472; 424/468; 424/438; 604/891.1
[58] Field of Search ............... 424/473, 472, 468, 438; 604/891.1

[56] References Cited

U.S. PATENT DOCUMENTS

| | | | |
|---|---|---|---|
| 3,133,132 | 11/1960 | Loeb et al. | 264/49 |
| 3,173,876 | 3/1960 | Zobrist | 252/137 |
| 3,276,586 | 8/1963 | Rosaen | 210/90 |
| 3,541,005 | 11/1970 | Strathmann et al. | 210/19 |
| 3,541,006 | 11/1970 | Bixler et al. | 210/23 |
| 3,546,142 | 12/1970 | Michaels et al. | 260/2.1 |
| 3,845,770 | 11/1974 | Theeuwes et al. | 128/260 |
| 3,865,108 | 2/1975 | Hartop | 128/260 |
| 3,916,899 | 11/1975 | Theeuwes et al. | 128/260 |
| 3,995,632 | 12/1976 | Nakano et al. | 128/260 |
| 4,002,173 | 1/1977 | Manning et al. | 128/296 |
| 4,111,202 | 9/1978 | Theeuwes | 128/260 |
| 4,160,020 | 7/1979 | Ayer et al. | 424/15 |
| 4,207,893 | 6/1980 | Michaels | 128/260 |
| 4,251,506 | 2/1981 | Laby | 424/19 |
| 4,327,725 | 5/1982 | Cortese et al. | 128/260 |
| 4,381,780 | 5/1983 | Holloway | 604/892 |
| 4,564,363 | 1/1986 | Bagnall et al. | 604/93 |
| 4,578,263 | 3/1986 | Whitehead | 424/15 |
| 4,595,583 | 6/1986 | Eckenhoff | 424/15 |
| 4,612,008 | 9/1986 | Wong et al. | 604/892 |
| 4,612,186 | 9/1986 | Eckenhoff et al. | 424/15 |
| 4,643,731 | 2/1987 | Eckenhoff | 604/892 |
| 4,703,118 | 11/1987 | Eckenhoff | 604/892 |
| 4,729,793 | 3/1988 | Eckenhoff | 106/169 |
| 4,772,474 | 9/1988 | Eckenhoff et al. | 424/465 |
| 4,783,337 | 11/1988 | Wong et al. | 424/468 |
| 4,824,675 | 4/1989 | Wong et al. | 424/438 |
| 4,865,598 | 9/1989 | Eckenhoff | 604/892.1 |
| 4,872,873 | 10/1989 | Zingerman | 604/892.1 |
| 4,874,388 | 10/1989 | Wong et al. | 604/891.1 |
| 4,876,093 | 10/1989 | Theeuwes et al. | 424/438 |
| 4,892,778 | 1/1990 | Theeuwes et al. | 428/218 |
| 4,915,949 | 4/1990 | Wong et al. | 424/438 |
| 4,927,419 | 5/1990 | Scully | 604/892.1 |
| 4,940,465 | 7/1990 | Theeuwes et al. | 604/892.1 |
| 5,023,088 | 6/1991 | Wong et al. | 424/473 |
| 5,045,082 | 9/1991 | Ayer et al. | 424/438 |

FOREIGN PATENT DOCUMENTS

| | | |
|---|---|---|
| 0025699 | 3/1981 | European Pat. Off. . |
| 0164241 | 12/1985 | European Pat. Off. . |
| 321043 | 6/1989 | European Pat. Off. . |
| WO86/00519 | 1/1986 | World Int. Prop. O. . |

Primary Examiner—Thurman K. Page
Assistant Examiner—Leon R. Horne
Attorney, Agent, or Firm—Jacqueline S. Larson; Steven F. Stone; Edward L. Mandell

[57] ABSTRACT

The present invention is directed to a long-term dispensing device for the controlled delivery of a beneficial agent in a hydrophilic carrier, which device quickly and continuously delivers an effective amount of agent followed by a continuous and sustained delivery of agent in a controlled and uniform amount over a prolonged period of time, thus providing for delivery of beneficial agent to an environment of use at two different rates and having a fast startup.

21 Claims, 2 Drawing Sheets

DUAL RATE AGENT DELIVERY DEVICE

FIELD OF THE INVENTION

The present invention pertains to the delivery of an active agent to an animal. More particularly, the invention is concerned with the continuous, controlled administration at a constant rate of an active agent from a hydrophilic formulation.

BACKGROUND OF THE INVENTION

Delivery devices for administering a beneficial agent to a biological fluid environment of use are known in the prior art. Representative examples of various types of delivery devices are disclosed in European publications EP 25,699 and 164,241 and in U.S. Pat. Nos. 3,995,632, 4,111,202, 4,251,506, 4,612,008, 4,824,675, 4,865,598, 4,872,873, 4,876,093, 4,892,778, 4,915,949, 4,940,465 and 5,023,088.

While the prior art delivery devices usually work successfully for their intended purpose, it has now been observed that the devices do not function well when the formulation to be dispensed is a hydrophilic beneficial agent formulation, that is, a beneficial agent formulation where the agent is combined with a hydrophilic carrier. When a hydrophilic agent formulation is dispensed from previous devices, uncontrolled release of the agent is often a problem, causing delivery of the agent into the environment of use in amounts and over periods of time that are not intended by the design of the device, and resulting in erratic or incorrect dosage profiles. This has been found to be particularly true in dynamic or vigorous environments such as active, grazing animals. Such uncontrolled release of a hydrophilic formulation has not been recognized or addressed in the prior art.

To overcome the limitations associated with the prior art delivery devices, a delivery device has been developed and is described and claimed in copending, commonly-assigned patent applications U.S. Ser. No. 07/641,023, filed Jan. 11, 1991, and U.S. Ser. No. 07/763,393, filed on Sep. 19, 1991, now U.S. Pat. No. 5,126,142 both to Ayer et al. This delivery device comprises a housing containing a beneficial agent such as an ionophore together with a hydrophilic carrier, an expandable driving member composition, and a densifier, the housing also having an exit passageway or a multiplicity of exit passageways, the diameter of each passageway being of a size to maximize release of the beneficial agent by osmotic pumping and minimize release of the beneficial agent by diffusion or erosion to substantially avoid mechanical agitation-dependent beneficial agent release. The expandable driving member absorbs liquid from the environment of use, expands and acts to drive out beneficial agent formulation from the interior of the device in a controlled manner for a prolonged period of time up to six months or longer.

While the device of U.S. Pat. No. 5,126,142 and No. 07/763,393 functions successfully to provide and maintain a controlled dosage of beneficial agent to the environment of use for an extended period of time, the device has the disadvantage of exhibiting a significant startup time between administration of the device to the subject animal or human and the onset of agent delivery at the desired rate.

Provision of effective dosages upon administration of the device can be obtained by prehydration (i.e., soaking) of the device prior to administration. For example, a device which exhibits a three-week delay prior to onset of effective delivery of the desired agent can be soaked for three weeks prior to administration to the subject. Effective delivery of the desired agent thus begins upon administration. However, prehydration of a long-term device has several significant disadvantages. The soaking of a single device for a period of three weeks requires a processing step which is undesirable, but it is likely to be manageable. However, the soaking of sufficient individual devices with which to supply an entire herd of animals can require a container the size of a swimming pool or a small lake. Also, the active agent which is being delivered by the device is distributed into the water in which the device is soaked, and can require special treatment of the water before it can be released into ground or sewage waters. Additionally, if the device has a limited lifespan (i.e., decomposition of the semipermeable membrane, density means, or other component of the device takes place over time), the time during which the device is prehydrated may limit the effective use in the subject animal.

The teachings of the prior art pertaining to loading doses of beneficial agent regarding short-term delivery devices do not provide a solution to the problem of the startup delay in long-term devices. An example of instantaneous delivery of agent from a short-term device is shown in U.S. Pat. No. 4,643,731, whereby instantaneous concentration of agent is obtained by providing a loading dose, i.e., an initial, immediate, short-term dose of beneficial agent, prior to the onset of the continuous delivery provided by the osmotic pump device. Due to the kinetics of the release of loading doses for short-term devices, the loading doses are active for only a short time and do not sustain the concentration of beneficial agent during the startup period demonstrated by long-term devices. Those loading doses provided within the coating of a short-term device are not appropriate for use with long-term devices having a semipermeable mebrane, as such coatings can interfere with the permeability of the semipermeable membrane and thus interfere with the operation of the device.

SUMMARY OF THE INVENTION

It is therefore an object of the present invention to provide a long-term dispensing device for the controlled delivery of a beneficial agent in a hydrophilic carrier, which device quickly and continuously delivers an effective amount of agent followed by a continuous and sustained delivery of agent in a controlled and uniform amount over a prolonged period of time.

Another object of the invention is to provide an improvement over the prior art by making available a dispensing device possessing controlled agent availability during a period of time which the prior art dispensing devices did not make agent available to the environment of use.

These and other objects are met by the present invention which is directed to a delivery device for dispensing a beneficial agent to an environment of use at two different rates and having a faster startup, where the device comprises:

a) a housing comprised of a wall surrounding an internal compartment, the wall being semipermeable in at least a portion;

b) a first beneficial agent formulation, comprising a first beneficial agent and a pharmaceutically acceptable hydrophilic carrier, in the compartment;

c) a second beneficial agent formulation, comprising a second beneficial agent and a pharmaceutically acceptable hydrophilic carrier, in the compartment;

d) a first exit means within that portion of the wall of the housing in contact with the first beneficial agent formulation, the exit means comprising an exit passageway or a multiplicity of exit passageways, the diameter of each passageway being of a size to provide rapid and continued delivery of the first beneficial agent for a first time period;

e) a second exit means in the compartment between the first beneficial agent formulation and the second beneficial agent formulation, the second exit means comprising an exit partition layer having an exit passageway or a multiplicity of exit passageways, the diameter of each passageway being of a size for maximizing the release of the second beneficial agent by osmotic pumping and minimizing the release of the beneficial agent by diffusion or erosion to provide continuous and sustained delivery in a controlled and uniform manner over a prolonged period of time;

f) an expandable driving member in the compartment; and g) optionally, a density element.

The invention is also directed to a method for delivering a beneficial agent to an environment of use quickly and continuously, followed by sustained delivery of the agent at a controlled and uniform rate over a prolonged period of time.

BRIEF DESCRIPTION OF THE DRAWINGS

In the drawing figures, which are not drawn to scale but are set forth to illustrate various embodiments of the invention, the drawing figures are as follows.

DETAILED DESCRIPTION OF THE INVENTION

Figure 1:
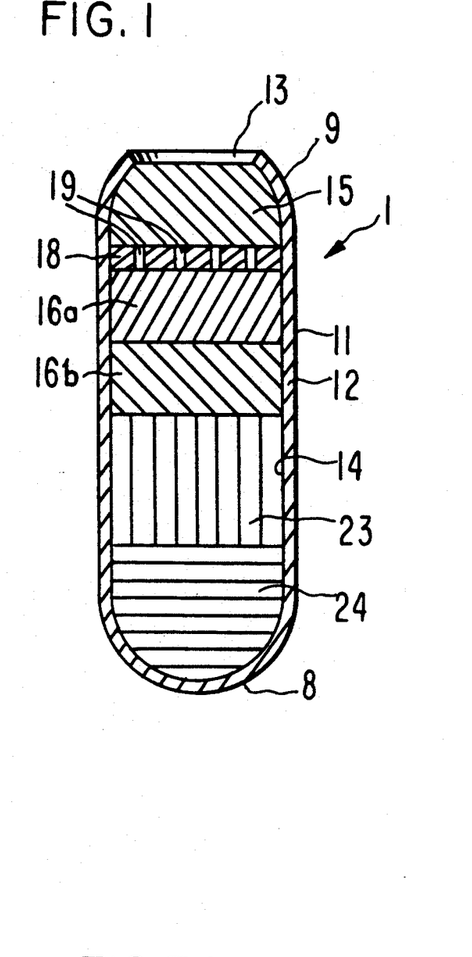
FIG. 1 is an opened view of a dosage form or dispensing device according to the present invention for administering a beneficial agent and hydrophilic carrier to a fluid environment of use.

One example of a dispensing device of the present invention is illustrated in FIG. 1. In FIG. 1, device 1 is seen in opened section and comprises lead end 9, rear end 8, a body 11, and a wall 12 that surrounds and forms an internal compartment 14 that communicates through a first exit means, in this embodiment a wide exit passageway 13, with the exterior of device 1. The first exit means is of a size that is large enough to provide for immediate initiation of delivery of a beneficial agent by diffusion or erosion of the beneficial agent formulation once the device 1 is placed into the environment of use. Wall 12 comprises totally a semipermeable composition, or wall 12 comprises at least in part a semipermeable composition. The remainder of wall 12, in the latter embodiment, may comprise a composition that is substantially nonpermeable to the passage of an exterior fluid present in the environment of use. Both semipermeable and nonpermeable portions of wall 12 are substantially impermeable to the passage of ingredients present inside device 1, and are non-toxic and maintain physical and chemical integrity during the delivery of the beneficial agent from device 1.

Internal compartment 14 comprises a first beneficial agent formulation 15 and a second beneficial agent formulation 16, which second formulation in device 1 is shown as two agent formulation layers or tablets 16a and 16b. While two layers of second agent formulation are illustrated, the number of layers or formulations is not critical and may be any number. The first agent formulation 15 comprises a first beneficial agent and a pharmaceutically acceptable hydrophilic carrier, and the second agent formulation 16 comprises a second beneficial agent and a pharmaceutically acceptable hydrophilic carrier. The first and second beneficial agents may be the same agent or different agents. The first and second formulations may comprise like or unlike agents. In a presently preferred embodiment, the formulations all comprise the same beneficial agent. The first and second formulations may comprise the same dosage unit amounts or the formulations may comprise different dosage unit amounts of an agent. The hydrophilic carriers can be the same or different in formulations 15 and 16. In all embodiments, the hydrophilic carriers imbibe and/or absorb an external fluid that enters compartment 14 and form thereby a dispensable composition for transporting the first and second beneficial agents from delivery device 1. The agent formulations in a preferred optional embodiment further comprise a composition-forming member such as a binder, a tableting agent or a lubricant. The composition-forming members can be the same or they can be different in formulations 15 and 16.

Delivery device 1 further comprises a second exit means in compartment 14, the second exit means comprising an exit partition layer 18 having a multiplicity of exit passageways 19. The diameter of each of the exit passageways 19 is of a size to maximize release of a beneficial agent by osmotic pumping and minimize release of a beneficial agent by diffusion or erosion to substantially avoid mechanical agitation-dependent beneficial agent release. Exit partition layer 18 is in preferably slideable arrangement in compartment 14 between first beneficial agent formulation 15 and second beneficial agent formulation 16. The exit passageways 19 are positioned in exit partition layer 18 in such manner that all of the exit passageways will be in communication with the environment of use through the first exit passageway 13 when the slideable exit partition layer 18 is pushed to lead end 9 after delivery device 1 is activated and first formulation 15 is delivered into the environment of use. In this way, beneficial agent from formulations 16a and 16b are displaced through exit passageways 19 into the environment of use.

Delivery device 1 in compartment 14 further comprises an expandable driving member 23 that is in contact with second agent composition 16. Expandable driving member 23 has a shape that corresponds to the internal shape of compartment 14. Expandable driving member 23, in the presence of an external fluid that enters compartment 14 through the semipermeable wall, imbibes and/or absorbs the fluid, increases in size, and thereby pushes against second agent formulation 16 to assist in displacing first formulation 15 from device 1 through exit passageway 13, to then slideably position second exit means 18 next to exit passageway 13, and to displace second formulation 16 from device 1 through exit passageways 19 and exit passageway 13.

Compartment 14 also comprises a density member or densifier 24 that is in contact with expandable driving member 23. Density member 24 is an important component of delivery device 1 when the delivery device is used in a presently preferred embodiment as a ruminal bolus, for keeping device 1 in the rumen of an animal over a prolonged period of time.

Figure 2:
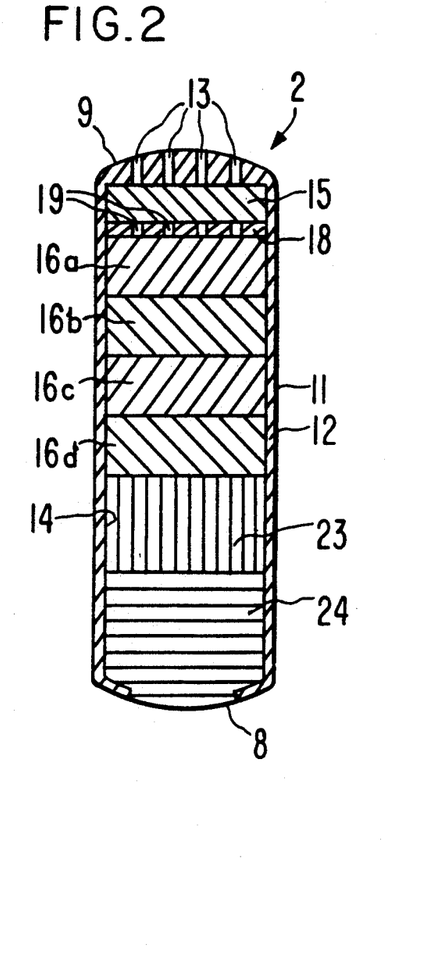
FIG. 2 is an opened view of another delivery device provided by the invention sized and adapted for administering a beneficial agent and hydrophilic carrier to a fluid environment of use.

FIG. 2 depicts, in opened view, another manufacture provided by the invention. In FIG. 2, delivery device 2 comprises a body 11 and a wall 12 that surrounds and forms internal lumen or compartment 14. Internal compartment 14 comprises first beneficial agent formulation 15, which formulation 15 comprises a pharmaceutically acceptable hydrophilic carrier containing a first beneficial agent, and second beneficial agent 16, which formulation 16 comprises a pharmaceutically acceptable hydrophilic carrier containing a second beneficial agent. In this embodiment, second agent formulation 16 is present as four agent formulation layers or tablets 16a, 16b, 16c and 16d, although the number is not controlling and any number of layers or formulations can be utilized. The beneficial agent in each of formulations 15 and 16 may be the same beneficial agent or different beneficial agents. In a presently preferred embodiment, the first and second agents are the same.

Figure 3A:
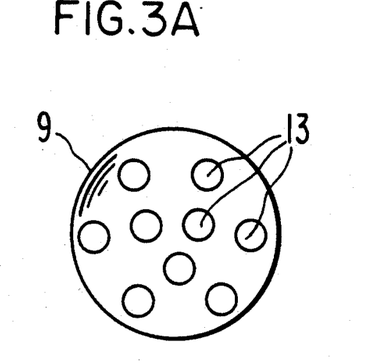
FIGS. 3A and 3B are top views of the exit means of the device of FIG. 2, FIG. 3A being a top view of the first exit means in the lead end and FIG. 3B being a top view of the slideable exit partition layer of the second exit means, illustrating a multiplicity of exit passageways in each of the exit means.
Figure 3B:
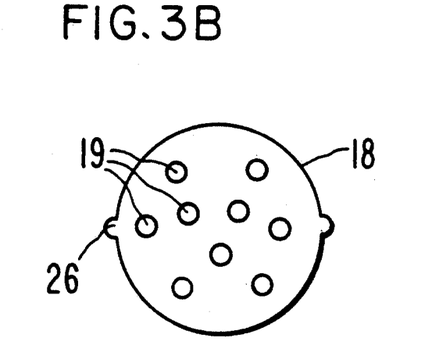

Compartment 14 also comprises expandable member 23. A densifier 24 is present in device 2 positioned distant from lead end 9, which in this embodiment is flattened in shape. Device 2 comprises a multiplicity of first exit passageways 13 in wall 12 at lead end 9. First exit passageways 13 comprise a number or multiplicity of openings, generally in a shower-head or screen-like arrangement. Delivery device 2 also includes a second exit means comprising a slideable exit partition layer 18 positioned between first beneficial agent formulation 15 and second beneficial agent formulation 16 and having a multiplicity of second exit passageways 19. Second exit passageways 19 are disposed in the same arrangement or distribution as the first exit passageways 13 so that when exit partition layer 18 is pushed against lead end 9 by the action of expandable member 23, the smaller second exit passageways 19 will align under the larger first exit passageways 13 for delivering second beneficial agent formulation 16 to the environment of use. One example of a possible configuration is illustrated in FIGS. 3A and 3B. FIG. 3A is a top view of lead end 9 of device 2 showing an arrangement of nine orifices or first exit passageways 13, each passageway being 100 mil in diameter. FIG. 3B is a top view of slideable exit partition layer 18 of device 2 showing an identical arrangement of nine orifices or second exit passageways 19 corresponding to the arrangement of first passageways 13 in lead end 9, except that each passageway 19 is smaller in size, being 60 mil in diameter. To assist in keeping second exit passageways 19 in correct alignment with first exit passageways 13, alignment means may be included in device 2, such as one or more protrusions 26 (in FIG. 3B) extending from the side of exit partition layer 18, which protrusions fit into grooves running longitudinally along the inner wall of compartment 14.

The delivery device or dispenser of the present invention can be sized and shaped for administering a beneficial agent to a variety of animals. In a presently preferred embodiment, the delivery device can be adapted for delivering an ionophore to ruminant animals including cattle, sheep, giraffes, deer, goats, bison and camels, and more particularly cattle and sheep, that comprise an important group of animals that require periodic administration of an ionophore. The delivery device can embrace a capsule-like shape and in one design have a diameter of from about 0.5 inches to about 1 inch (about 1.3 cm to about 2.5 cm) and a length of from about 0.5 inches to about 2.5 inches (about 1.3 cm to about 6.6 cm). For use with cattle, the delivery device has a diameter of from about 0.5 inches to about 1.5 inches (about 1.3 cm to about 3.8 cm), and a length of from about 1 inch to about 4 inches (about 2.5 cm to about 10.2 cm).

While FIGS. 1 through 3 illustrate various dosage forms that can be made according to the invention, it is to be understood that these devices are not to be construed as limiting the invention, as the device can take other shapes, sizes and forms for delivering a beneficial agent to a biological environment of use. The delivery device may be used to deliver an agent to animals including warm-blooded animals, mammals and humans. The delivery device can be used in veterinary clinics, farms, zoos, laboratories, on the range, in feed lots, and other environments of use. The delivery device can be used for dispensing a beneficial agent formulation to a fluid environment of use, wherein the fluid environment is an aqueous environment, which aqueous environment includes biological aqueous-type fluids. The presently preferred environment of use comprises the rumen of a ruminant animal. However, the devices are not restricted to use in ruminant animals or to a rumen environment of use. The environment of use can comprise a body cavity such as the peritoneum, vagina, or intestinal tract. The device may also be utilized as a subcutaneous implant. A single dispensing device or several dispensing devices can be administered to a subject during a therapeutic program.

The terms "exit means" and "exit passageway", as used herein, comprise means and methods suitable for the metered release of a hydrophilic composition comprising beneficial agent from compartment 14 of the delivery device of the present invention. The exit means includes at least one passageway, orifice, or the like for communicating the internal compartment with the environment of use. The invention provides a passageway for releasing a composition intact and it also provides a passageway means, such as a multiplicity of passageways, for dividing the original composition into smaller compositions as it is released from the delivery device. The release of a composition from the device, in either instance, embodies a combination of osmotic hydrodynamic pumping and diffusion or erosion properties through an exit passageway or through a multiplicity of exit passageways functioning as an exit port. The delivery rate is influenced not only by the rate at which the osmotic pump of the device pushes the composition into the environment of use, but also by the nature of the composition and its interaction with fluid at the interface with the environment of use. The interface provides an exterior mechanical action that controls drug released by the environment and not by the device.

It has been found that in prior art devices, excessive diffusion or erosion of the hydrophilic formulation at the orifice of the exit passageway caused a lack of controlled release by creating mechanical agitation-dependent beneficial agent diffusion or erosion and release that could vary greatly from the desired rate. When the diffusion or erosion is increased, more agent is released per unit time, and the amount can vary depending on various parameters of the environment of use, such as, for example, the amount of agitation of the environment and the amount and types of other matter in the environment (which matter can come into contact with the agent composition and erode the composition, much in the manner of sandpaper). This is particularly a problem when the environment of use is dynamic and vigorous, such as active grazing livestock or livestock kept together in penned groups, or animals grazing on open lands, which grazing picks up foreign matter such as dirt and wire in addition to vegetation. In order to obtain a controlled release at a constant rate, such excessive diffusion or erosion must be eliminated.

Figure 4:
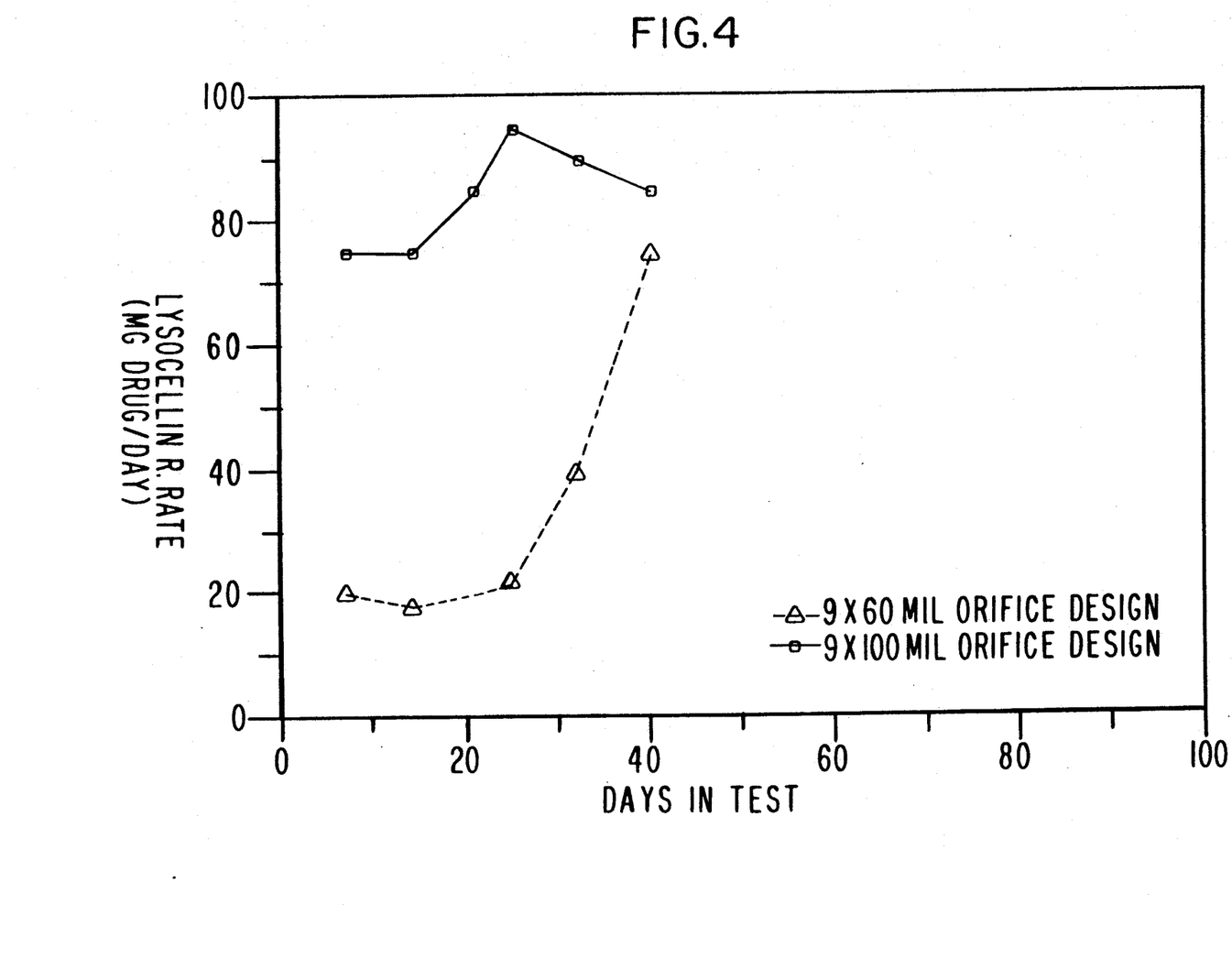
FIG. 4 is a graph that presents the in vitro release rate profiles of two prior art delivery devices over the first 40 days of delivery, the rates determined by gravimetric analysis.

At the same time, devices having an osmotic expandable member, as in the present invention, require a "startup" period of time, usually of at least several days and often of up to several weeks, for the expandable member to become activated and begin to push against the beneficial agent formulation to deliver beneficial agent to the environment of use at the desired constant rate. Additionally, with smaller-sized orifices, it takes a longer time for the hydrophilic agent formulation to hydrate and become dispersable. As a result of the startup period of the osmotic expandable member and the slower hydration of the agent formulation, there is a significant lag time before the device begins to deliver agent at a steady state. This is illustrated in FIG. 4, which presents the release rate profiles obtained in vitro of devices containing a lysocellin/hydrophilic formulation designed to deliver 80 mg/day of lysocellin, the devices being those disclosed in U.S. Pat. No. 5,126,142 prior application U.S. Ser. No. 07/763,393. The profile for a device having nine orifices of 100 mil each (indicated by squares and solid line) shows that delivery of the target amount of drug is almost immediate; however, the delivery is variable rather than being at a constant rate. The profile for a device having nine orifices of 60 mil each (indicated by triangles and dotted line) shows a slow start-up of delivery of the drug from the system.

The present invention addresses and solves the problems of erratic, uncontrolled release and slow startup by providing, in accordance with the practice of the invention, a first exit means for the immediate and continued delivery of active agent during the period required for the expandable driving member to become activated (the "first time period"), after which the invention provides a second exit means for maximizing the release of the beneficial agent by osmotic pumping and minimizing the release of the beneficial agent by diffusion or erosion to provide continuous and sustained delivery in a controlled and uniform manner over a second prolonged period of time. In this manner, beneficial agent is provided quickly to the environment of use for a relatively short period of time until the osmotic driving member can become activated to then begin delivery of beneficial agent in a controlled manner for the remaining prolonged life of the device.

Such exit means have been found to be related to the size of the orifice of the exit passageway. It has been discovered that the size of the exit orifice or, in other words, the surface area of hydrophilic composition exposed to the environment of use, is one of the major factors contributing to the diffusion or erosion action and thus is critical to controlling such diffusion. The surface area for exit passageways of differing diameters is presented in Table A.

TABLE A

| Exit passageway diameter mils | Exit passageway surface area cm² |
|---|---|
| 60 × 9* | 0.164 |
| 85 × 9* | 0.329 |
| 100 | 0.051 |
| 200 | 0.203 |
| 300 | 0.456 |
| 100 × 9* | 0.456 |
| 400 | 0.810 |

*9 passageways of 60, 85, or 100 mils each

The diffusional/erosional release increases with an increase in the exit diameter. To illustrate, for nine orifices of 100 mil exit diameter each or for one orifice of 300 mil exit diameter, the diffusional release of a lysocellin hydrophilic formulation is 21.5%, whereas for one 400 ml exit orifice, with the same agent formulation, the diffusional release is 33% of the total release rate.

Thus, the delivery device provided by this invention comprises one exit passageway or a multiplicity of exit passageways, the "first exit means", the diameter of each first exit passageway 13 being of a greater size to provide for immediate diffusion or erosion of a first beneficial agent formulation into the environment, the diffusion or erosion being primarily as a result of mechanical agitation and substantially independent of the osmotic pumping action of the expandable member. It has now been found that, generally, the diameter of each first exit passageway is preferably of about 100 mil or larger.

The amount of first beneficial agent formulation 15 present in the delivery device will be an amount that is sufficient to provide beneficial agent to the environment primarily by erosion or diffusion for the entire startup period of the osmotic expandable member but will be essentially all released to the environment at such time as the expandable member becomes completely activated.

The delivery device further comprises one exit passageway or a multiplicity of exit passageways, the "second exit means", the diameter of each second exit passageway 19 being of a size to maximize the release of agent by osmotic pumping and minimize the release of agent by diffusion or erosion, thereby substantially avoiding mechanical agitation-dependent drug release. The diameter of the second exit passageway or passageways necessary to provide maximum osmotic pumping and minimum diffusion or erosion from the device of the invention is dependent on several factors, such as the solubility of the beneficial agent and the hydrophilic carrier in the environment of use and the desired amount of the agent to be delivered into the environment. However, it has been found that there is generally a preferred diameter size, which size is less than 100 mil, usually of from about 95 mil to about 60 mil, more preferably of from about 80 mil to about 60 mil, most preferred being about 75 mil. With an exit orifice of about 100 mil diameter or greater, release due to diffusion or erosion will be great enough to cause a loss of controlled release of the composition, whereas an exit orifice of less than about 60 mil will be too small to allow adequate passage of the highly viscous hydrophilic composition from the device.

In those cases where one exit passageway of the appropriate diameter is not sufficient to allow delivery of the beneficial agent composition in the required amounts, it is preferred to provide a multiplicity of exit passageways of appropriate diameter, the number and size of passageways being such as to be sufficient, in the aggregate, to deliver the agent in the required amounts per unit of time. Such numbers and sizes can be determined with a minimum of effort based on the knowledge in the drug delivery art and on the disclosure herein.

To provide a second exit means, the device of the present invention includes a second exit partition layer 18 between the first beneficial agent formulation 15 and the second beneficial agent formulation 16. The exit partition layer 18 includes the second exit passageway or multiplicity of second exit passageways 19, and the exit partition layer is preferably slideable within the internal compartment of the device. The exit partition layer 18 will be positioned in the compartment such that the second exit passageway or passageways align with the first exit passageway or passageways, allowing the second beneficial agent formulation to exit unimpeded through the passageways from the device into the environment.

Second exit partition layer 18, positioned between the first beneficial agent formulation and the second beneficial agent formulation, may be comprised of a semipermeable material or an impermeable material. Representative materials useful as an exit partition layer 18 are known in the art and may be selected from those materials comprising the wall 12. Additional representative materials are given in, for example, U.S. Pat. No. 4,874,388.

Wall 12 comprises a wall-forming composition that does not adversely affect the host and does not adversely affect the beneficial agent and other ingredients in the delivery device of this invention. Wall 12 in at least a part is semipermeable; that is, the wall is permeable to the passage of an external fluid such as water and biological fluids and is substantially impermeable to the passage of beneficial agent. In a preferred embodiment, all of wall 12 is semipermeable.

Typical materials used for forming wall 12 are, in one embodiment, cellulose esters, cellulose ethers, and cellulose esterethers. The cellulose polymers have a degree of substitution, D.S., on their anhydroglucose unit of from greater than 0 up to 3, inclusive. By "degree of substitution" is meant the average number of hydroxyl groups originally present on the anhydroglucose unit comprising the cellulose polymer that are replaced by a substituting group. Representative materials include a member selected from the group consisting of a cellulose acylate, cellulose diacylate, cellulose triacylate; cellulose acetate, cellulose diacetate, cellulose triacetate; mono-, di-, and tricellulose alkanylates; mono-, di-, and tricellulose aroylates; and the like. Exemplary polymers include cellulose acetate having a D.S. up to 1 and an acetyl content up to 21%; cellulose acetate having a D.S. of 1.8 to 2.3 and an acetyl content of 32% to 39%; cellulose diacetate having a D.S. of 1 to 2 and an acetyl content of 21% to 35%; cellulose triacetate having a D.S. of 2 to 3 and an acetyl content of 34% to 44.8%; and the like. More specific cellulose polymers include cellulose propionate having a D.S. of 1.8, a propyl content of 39.2% to 45% and a hydroxyl content of 2.8% to 5.4%; cellulose acetate butyrate having a D.S. of 1.8, an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose triacylate having a D.S. of 2.9 to 3 such as cellulose trivalerate, cellulose trilaurate, cellulose tripalmitate, cellulose trisuccinate and cellulose trioctanoate; cellulose diacylate having a D.S. of 2.2 to 2.6 such as cellulose disuccinate, cellulose dipalmitate, cellulose dioctanoate and cellulose dipentanoate; coesters of cellulose such as cellulose acetate butyrate and cellulose acetate propionate; and the like.

Additional polymers include ethyl cellulose of various degrees of etherification with ethoxy content of from 40% to 55%; cellulose acetate ethyl carbamate; cellulose acetate methyl carbamate; cellulose acetate diethyl aminoacetate; semipermeable polyurethanes; semipermeable sulfonated polystyrenes; semipermeable cross-linked polymers formed by the coprecipitation of a polyanion and a polycation as disclosed in U.S. Pat. Nos. 3,173,876, 3,276,586, 3,541,005, 3,541,006, 3,546,142, 4,595,583 and 4,783,337; and the like. Semipermeable polymers also are disclosed by Loeb and Sourirajan in U.S. Pat. No. 3,133,132. Semipermeable lightly cross-linked polymers, semipermeable cross-linked poly(sodium styrene sulfonate), semipermeable cross-linked poly(vinylbenzyltrimethyl) ammonium chloride, semipermeable polymers exhibiting a fluid permeability of $2.5 \times 10^{-8}$ to $2.5 \times 10^{-3}$ (cm$^2$/hr.atm) expressed per atmosphere of hydrostatic or osmotic pressure difference across a semipermeable membrane are disclosed in U.S. Pat. No. 3,845,770, 3,916,899 and 4,160,020; and in "Handbook of Common Polymers" by Scott, J. R. and Roff W. J. (1971), published by CRC Press, Cleveland, OH.

Semipermeable wall 12 also can comprise a flux-regulating agent. The flux-regulating agent is a compound that assists in regulating the permeability of a fluid through the semipermeable wall. Flux-regulating agents that increase the permeability of a wall to fluid, such as water, are essentially hydrophilic. The amount of regulator in the wall, when incorporated therein, generally is from about 0.01 weight percent (wt %) to 35 wt % or more. The fluxregulator agents in one embodiment comprise a member selected from the group consisting of a polyhydric alcohol, polyalkylene glycol, polyalkylenediol, polyester of alkylene glycol, and the like. Typical flux enhancers comprise polyethylene glycol 300, 400, 600, 1500, 4000, 6000, and the like; low molecular weight glycols such as polypropylene glycol, polybutylene glycol, and polyamylene glycol; the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol, and the like; esters such as ethylene glycol dipropionate, ethylene glycol butyrate, butylene glycol dipropionate, and the like.

Semipermeable wall 12 optionally comprises a plasticizer, for imparting flexibility and elongation properties to the wall, for making the wall less- to non-brittle, and for enhancing the manufacturing properties of the wall. Plasticizers useful for the present purpose comprise dihexyl phthalate, butyl octyl phthalate, triacetin, dioctyl azelate, epoxidized tallate, sucrose acetate isobutyrate, epoxidized soybean oil, citric acid esters, phosphate esters, tricresyl phosphate, triacetyl phosphate, adipate esters, sebacate esters, and other nontoxic plasticizers. The amount of plasticizer in wall 12, when incorporated therein, is about 0.01 wt % to 40 wt % or more.

The term "beneficial agent" as used herein denotes any beneficial agent or compound that can be delivered by the delivery device of the present invention to produce a beneficial and useful result. The beneficial agent can be from very soluble to insoluble in the hydrophilic carrier. The term "beneficial agent" includes, but is not limited to, biocides, parasiticides, fungicides, larvicides, medicinals, drugs, nutrients, vitamins, food supplements, minerals, anthelmintics, anti-infestation agents, growth promotants, ionophores, and other agents that benefit the environment of use. The terms "beneficial agent", "agent" and "drug" are used interchangeably herein.

The agents or drugs can be in various forms, such as uncharged molecules, molecular complexes, and pharmacologically acceptable salts. Derivatives of compounds, such as esters, ethers amides, and the like, can be used. The amount of agent or drug present in a device generally can be from about 0.05 ng to 5 g or more. The devices of the invention can dispense from 0.1 to 1500 mg/hr. The devices can dispense agent from 1 day to 6 months or more.

In a presently preferred embodiment of the present invention, the beneficial agent is an ionophore. Beneficial ionophores that can be dispensed using the delivery device of this invention comprise natural and synthetic ionophores. The ionophores are polyethers and they possess the ability to transport mono- and divalent cations across lipid bilayers which lie within biological membranes. The ionophores possess unique properties which derive from their ability to perturb transmembrane ion gradients and electrical potentials. The ability of ionophores to complex and transport ions leads to their applications as antibiotics against gram-positive microorganisms, against mycobacteria, as growth promotants in ruminants such as cattle and sheep, and for improved feed utilization as seen by increasing the efficiency of meat production. Ionophores that can be stored and dispensed by the dosage form of this invention comprise a member selected from the group consisting of azolomycin, valinomycin, enniactin, monactin, nonactin, dinactin, trinactin, virginiamycin, tetronasin, semduramicin, monensin, monensin sodium, monensin factor B, monensin factor C, nigericin, narasin also known as methyl salinomycin, salinomycin, isolasalocid, lasalocid, lysocellin, septamycin, laidlomycin, laidlomycin propionate, laidlomycin butyrate, lonomycin, lenotemycin, grisorixin, ferensimycin, alborixin, rosgramicin, erythromycin, sodium lysocellin, and the like. The polyethers include bambermycin, monenomycin, flavomycin, and the like. The ionophores also comprise the pharmaceutically acceptable derivatives having ionophore activities, such as the pharmaceutically acceptable salts, the alkyl and alkenyl derivatives, the monoglycoside and diglycoside derivatives, the hydroxylated derivatives, the free acid, the hydrate, the ester derivatives, the ether derivatives, and the like. In one presently preferred embodiment, the ionophores exhibit a molecular weight of about 350 to 2500.

The beneficial agent is present in the invention in a therapeutically effective amount; that is, in an amount that is necessary to provide a desired therapeutic, usually beneficial, effect for the effective life of the device. The presently preferred amount of an ionophore in a dosage form, present in a single composition, in first and second compositions, or in first, second and third compositions, or the like, generally is from about 10 milligrams to 100 grams, preferably from about 10 milligrams to 30 grams. The amount of ionophore in a first and a second composition or in a first, a second and a third composition, or the like, can be the same or different, with the total amount of ionophore in all compositions in the dispenser equal to a maximum of 100 g, and preferably to a maximum of 30 g. The first, second and/or third compositions can comprise one or more than one like or unlike ionophores. The delivery device provided by the invention can deliver various dosage amounts of an ionophore, for example, from 10 mg per day to 500 mg per day, for 150 days or longer. The ionophores are known in the ionophore art in "Kirk-Othmer Encyclopedia", Vol. 3, pp 47-64 (1978); Ann N.Y. Acad. Sci., Vol. 264, pp 373-86 (1975); and ACS Sym., Ser. 140, pp 1-22 (1980). The ionophore can be present as a base, as a salt, as an ester, or an another derivative thereof.

The pharmaceutically acceptable carriers forming the first and second formulations 15 and 16 and comprising the beneficial agent(s) comprise pharmaceutically acceptable polymers that are hydrophilic, nontoxic, and substantially free of reaction with a beneficial agent and other members forming the delivery device. The pharmaceutically acceptable hydrophilic carrier comprising a beneficial agent provides unexpected advantages such as (a) the ability to store a high dosage amount, up to 95 wt %, of an agent; (b) the ability to store a high dosage agent in controlled, small doses over a prolonged time up to about 5 or 6 months or longer; (c) the ability to substantially protect a fluid-sensitive agent from fluid that enters the delivery device, by harboring the agent within its polymeric structure; and (d) the ability to charge high loadings of an agent in a polymer carrier that undergoes change from a rested state to a dispensable state possessing a dispensable viscosity or to a semisolid dispensable state during operation of the dosage form. The polymer carriers useful for the present purpose can be chosen from, but are not limited to, a member selected from the group including polyethylene oxide polymers having a 100,000 to 7,500,000 molecular weight; carboxyvinyl polymers, sometimes referred to as carboxypolymethylene, commercially available as Carbopol ® polymer, possessing a 200,000 to 5,000,000 molecular weight; poly(vinyl pyrrolidone) having a 125,000 to 460,000 molecular weight; poly(hydroxyalkyl methacrylate) having a 100,000 to 5,000,000 molecular weight; polysaccharides such as agar, karaya, tragacanth, algin, guar, nanthan, and the like, having a 50,000 to 2,000,000 molecular weight; and the like.

Expandable driving member 23, operable for displacing the second agent formulation and assisting in displacing the first agent formulation from the delivery device, comprises, in a presently preferred embodiment, an osmopolymer or hydrogel composition. The hydrophilic osmopolymers interact with water and aqueous biological fluids and swell or expand to an equilibrium state. The osmopolymers exhibit the ability to swell in water and to retain a significant portion of the imbibed and absorbed water within the polymer structure. The osmopolymer is noncross-linked or optionally lightly cross-linked and it possesses osmotic properties such as the ability to imbibe an exterior fluid through the semipermeable wall and exhibit an osmotic pressure gradient across the semipermeable wall. The polymers in a preferred embodiment are gel polymers that can swell or expand to a very high degree, usually exhibiting a 2- to 50-fold volume increase, thereby pushing and displacing the composition comprising the beneficial agent from the delivery device. The polymers can be of plant, animal or synthetic origin. Polymeric materials useful for forming the expandable driving member comprise anionic and cationic hydrogels; polyelectrolyte complexes; a mixture of agar and carboxymethylcellulose; a composition comprising methylcellulose mixed with sparingly cross-linked agar; a water-swellable polymer of N-vinyl lactams; polyethylene oxide polymers possessing a 1,000,000 to 10,000,000 molecular weight; carboxyvinyl polymers (Carbopol ®); starch graft polymers; sodium carboxymethylcellulose having a 90,000 to 1,000,000 molecular weight; a composition comprising sodium carboxymethylcellulose and a member selected from the group consisting of hydroxypropylcellulose and hydroxypropylmethylcellulose; and the like. Representative polymers possessing hydrophilic properties are known in U.S. Pat. Nos. 3,865,108, 4,002,173, 4,207,893, and 4,327,725, and in *Handbook of Common Polymers* by Scott and Roff, published by the Cleveland Rubber Company, Cleveland, OH.

Expandable polymer driving member 23 optionally comprises, in addition, an osmotically effective compound dispersed within the polymer. Osmotically effective compounds also are known as osmotically effective solutes and as osmagents. The osmotically effective compounds exhibit an osmotic pressure gradient across semipermeable wall 12, and they imbibe fluid into compartment 14. The presence of this imbibed fluid provides added fluid for the expandable polymer to absorb and increase its volume, and the imbibed fluid continuously fills the driving area of the compartment and forms a push member that urges the first agent composition and the second agent composition from the delivery device. Osmotically effective compounds or solutes useful for the present purpose can be selected from, but are not limited to, magnesium sulfate, magnesium chloride, sodium chloride, potassium chloride, lithium chloride, potassium sulfate, sodium sulfate, mannitol, urea, sorbitol, inositol, sucrose, glucose, a mixture of sodium chloride and magnesium chloride, a mixture of potassium chloride and sucrose, and the like. The osmotic pressure in atmospheres, atm, of osmotically effective compounds suitable for the invention will be greater than zero atm, generally from eight atm up to 500 atm, or higher. The amount of osmotically effective compound blended homogeneously or heterogeneously with the swellable polymer is from about 0.02 wt % to 50 wt %. Osmotically effective solutes are known in the art, in for example U.S. Pat. Nos. 4,595,583 and 4,783,337.

Composition-forming members or tableting aids optionally used to provide the beneficial agent formulations may comprise, for example, binders that impart cohesive qualities to the composition such as poly(vinyl pyrrolidone), natural and synthetic gums such as sodium alginate, methylcellulose, hydroxypropylmethylcellulose, Veegum ®, waxes, and the like; lubricants for enhancing the rate of flow of the tablet granulation, to prevent adhesion to dies and punches during tableting processes, such as a magnesium stearate, calcium stearate, stearic acid, talc, lycopodium, and the like; coloring agents for esthetic qualities and identification such as FD&C Blue No. 1; surfactants that aid in dispensing the beneficial agent after its release from the dosage form, such as anionic, cationic, nonionic and amphoteric surfactants; and the like. Composition-forming members are disclosed in *Pharmaceutical Sciences*, Remington, 14th Ed. (1970). The amount of composition-forming member present in the formulation is from about 0.01 wt % to 20 wt %.

The density member or densifier 24 is used in the delivery device of the invention to retain the device in the rumen-reticular sac of a ruminant. Density member 24 allows the delivery device to remain in the rumen over a prolonged period of time, rather than letting it pass into the alimentary tract and be eliminated therefrom. As the device remains in the rumen, beneficial agent is delivered at a controlled rate to the ruminant over a prolonged period up to 6 months or longer. Generally, density member 24 will have a density of from about 1.0 to 8, or higher, with the density in a presently preferred embodiment exhibiting a specific gravity of from 1.5 to 7.6. For the ruminants cattle and sheep, it is presently preferred that density member 24 exhibit a density to assure complete system density of 2 to 3 or greater. Materials that have a density that can be used for forming densifier 24 include iron, iron oxide, iron shot, iron shot coated with iron oxide, iron shot magnesium alloy, steel, stainless steel, copper oxide, a mixture of copper oxide and iron powder, and the like. Density of the device may also be achieved by incorporation of barium sulfate. Density member 24 in the delivery device can embrace different embodiments. For example, densifier 24 can be machined or cast as a single, solid piece made of stainless steel having a density of 7.6. The solid member is made having a shape that corresponds to the internal shape of the device. Density member 24 in another manufacture can be a solid member having an axially aligned bore that extends through the length of the member to provide a first exit passageway 13. In another embodiment, density member 24 can comprise a plurality of dense pellets.

An embodiment of the invention pertains to a method for administering a beneficial agent such as an ionophore at a controlled rate to the rumen of a ruminant. In carrying out the method, a dispenser is placed into a balling gun provided with an ejecting means, the gun is inserted into the mouth of the animal beyond the base of the tongue, and the dispenser is gently ejected by applying pressure to an ejection plunger in the gun, thereby sending the dispenser into the rumen. More specifically the method comprises the steps of:

(1) admitting into an animal's rumen a dispenser comprising:

a) a housing comprised of a wall surrounding an internal compartment, the wall being semipermeable in at least a portion;

b) a first beneficial agent formulation, comprising a first beneficial agent and a pharmaceutically acceptable hydrophilic carrier, in the compartment;

c) a second beneficial agent formulation, comprising a second beneficial agent and a pharmaceutically acceptable hydrophilic carrier, in the compartment;

d) a first exit means within that portion of the wall of the housing in contact with the first beneficial agent formulation, the exit means comprising an exit passageway or a multiplicity of exit passageways, the diameter of each passageway being of a size to provide rapid and continued delivery of the first beneficial agent for a first time period;

e) a second exit means in the compartment between the first beneficial agent formulation and the second beneficial agent formulation, the second exit means comprising an exit partition layer having an exit passageway or a multiplicity of exit passageways, the diameter of each passageway being of a size for maximizing the release of the second beneficial agent by osmotic pumping and minimizing the release of the beneficial agent by diffusion or erosion to provide continuous and sustained delivery in a controlled and uniform manner over a prolonged period of time;

f) an expandable driving member in the compartment; and g) optionally, a density element;

(2) imbibing fluid through the semipermeable wall at a rate determined by the permeability of the wall and the osmotic pressure gradient across the wall, which fluid contacts the formulation comprising the beneficial agent to form a dispensable composition and contacts the expandable driving member to cause the expandable driving member to expand and push against the agent composition;

(3) quickly delivering the first beneficial agent from the compartment by the first beneficial agent formulation being dispensed in a beneficially effective amount through the first exit means by diffusion or erosion into the rumen for a first period of time; and (4) delivering the second beneficial agent from the compartment by the expandable driving member continually expanding against the second beneficial agent formulation and causing the beneficial agent to be dispensed in a beneficially effective amount through the second exit means at a controlled rate to the rumen over a prolonged period of time.

The following examples are merely illustrative of the present invention and they should not be construed as limiting the scope of the invention in any way, as these examples and other equivalents thereof will become more apparent to those skilled in the dispensing art in light of the present disclosure, the drawings and the accompanying claims.

EXAMPLE 1

A dispensing device for the delivery of lysocellin to livestock is made as follows. First, a semipermeable membrane cup having a composition of 79 wt % cellulose acetate butyrate (acetyl content 13% and butyryl content 37%), 15 wt % Citroflex ®-2 triethyl citrate and 6 wt % poly(ethylene glycol) 400 is injection-molded into a shape having a domed lead end and an opposite open end. Nine exit passageways (orifice channels) of 100 mil diameter each are molded into the lead end. Two grooves also are molded longitudinally into the inner wall of the membrane cup. The cup has dimensions of approximately 8.9 cm length, 2.5 cm width and 0.35 cm wall thickness.

An exit partition layer of the same composition as that of the membrane cup is prepared. The material is formed into a flattened disk of the same circumference as the inside circumference of the membrane cup and with two protrusions extending one on each side of the disk for fitting into the two longitudinal grooves in the membrane cup. Nine exit passageways (orifice channels) of 60 mil diameter each are molded into the exit partition disk in the same pattern as the passageways in the lead end of the membrane cup.

An ionophore composition comprising 82.0 wt % lysocellin, 16.0 wt % polyethylene oxide, 1.0 wt % hydroxypropylmethylcellulose E-5 and 1.0 wt % magnesium stearate is pressed into five solid tablets, each weighing 3.0 g.

One lysocellin tablet, which has been pressed on one face into a shape conforming to that of the domed end and with a flat second face, is inserted into the open end of the cup and seated against the lead end. The exit partition disk is then inserted behind the first lysocellin tablet, with the protrusions of the disk inserted in the longitudinal grooves of the cup so that the exit passageways of the disk are in alignment with the exit passageways of the cup. The second lysocellin tablet is then inserted behind the disk, and the third, fourth and fifth tablets are inserted behind the second. Each of these four tablets has two flat faces.

Next, 9.1 g of a hydrophilic expandable tablet is formed, the tablet having the following composition: 63.0 wt % sodium carboxymethylcellulose, 30.0 wt % sodium chloride, 4.75 wt % hydroxypropylcellulose EF, 1.0 wt % hydropropylmethylcellulose E-5, 1.0 wt % ferric oxide, and 0.25 wt % magnesium stearate. The expandable tablet is inserted in to the semipermeable membrane cup behind the fifth ionophore tablet.

A stainless steel density element (73 g) having a density of 7.7 g/cc is then placed in the membrane cup behind the expandable tablet. The protruding lip of the cup is heated until softened and the lip is crimped over the perimeter of the density element to provide the dispenser.

Inasmuch as the foregoing specification comprises presently preferred embodiments of the invention, it is to be understood that various improvements and modifications may be made herein in accordance with the inventive principles disclosed without departing from the scope of the invention.

What is claimed is:

1. A delivery device for dispensing a beneficial agent to an environment of use at two different rates and having a faster startup, where the device comprises:

a) a housing comprised of a wall surrounding an internal compartment, the wall being semipermeable in at least a portion;

b) a first beneficial agent formulation, comprising a first beneficial agent and a pharmaceutically acceptable hydrophilic carrier, in the compartment;

c) a second beneficial agent formulation, comprising a second beneficial agent and a pharmaceutically acceptable hydrophilic carrier, in the compartment;

d) a first exit means within that portion of the wall of the housing in contact with the first beneficial agent formulation, the exit means comprising an exit passageway or a multiplicity of exit passageways, the diameter of each passageway being of a size to provide rapid and continued delivery of the first beneficial agent for a first time period;

e) a second exit means in the compartment between the first beneficial agent formulation and the second beneficial agent formulation, the second exit means comprising an exit partition layer having an exit passageway or a multiplicity of exit passageways, the diameter of each passageway being of a size for maximizing the release of the second beneficial agent by osmotic pumping and minimizing the release of the beneficial agent by diffusion or erosion to provide continuous and sustained delivery in a controlled and uniform manner over a prolonged period of time; and f) an expandable driving member in the compartment.

2. A delivery device according to claim 1 wherein the first beneficial agent and the second beneficial agent are the same beneficial agent.

3. A delivery device according to claim 1 wherein the beneficial agent is an ionophore.

4. A delivery device according to claim 2 wherein the beneficial agent is an ionophore.

5. A delivery device according to claim 3 wherein the ionophore is lysocellin, lasalocid, tetronasin or laidlomycin propionate.

6. A delivery device according to claim 4 wherein the ionophore is lysocellin, lasalocid, tetronasin or laidlomycin propionate.

7. A delivery device according to claim 1 wherein the diameter of each of the first exit passageways is 100 mil or larger, and the diameter of each of the second exit passageways is from about 60 mil to about 95 mil.

8. A delivery device according to claim 7 wherein the beneficial agent is an ionophore.

9. A delivery device according to claim 8 wherein the first beneficial agent and the second beneficial agent are the same ionophore, and the ionophore is chosen from lysocellin, lasalocid, tetronasin and laidlomycin propionate.

10. A method for dispensing a beneficial agent to an environment of use at two different rates and having a faster startup, the method comprising the steps of:

(1) admitting into the environment of use a dispenser comprising:
  a) a housing comprised of a wall surrounding an internal compartment, the wall being semipermeable in at least a portion;
  b) a first beneficial agent formulation, comprising a first beneficial agent and a pharmaceutically acceptable hydrophilic carrier, in the compartment;
  c) a second beneficial agent formulation, comprising a second beneficial agent and a pharmaceutically acceptable hydrophilic carrier, in the compartment;
  d) a first exit means within that portion of the wall of the housing in contact with the first beneficial agent formulation, the exit means comprising an exit passageway or a multiplicity of exit passageways, the diameter of each passageway being of a size to provide rapid and continued delivery of the first beneficial agent for a first time period;
  e) a second exit means in the compartment between the first beneficial agent formulation and the second beneficial agent formulation, the second exit means comprising an exit partition layer having an exit passageway or a multiplicity of exit passageways, the diameter of each passageway being of a size for maximizing the release of the second beneficial agent by osmotic pumping and minimizing the release of the beneficial agent by diffusion or erosion to provide continuous and sustained delivery in a controlled and uniform manner over a prolonged period of time; and
  f) an expandable driving member in the compartment;

(2) imbibing fluid through the semipermeable wall at a rate determined by the permeability of the wall and the osmotic pressure gradient across the wall, which fluid contacts the formulation comprising the beneficial agent to form a dispensable composition and contacts the expandable driving member to cause the expandable driving member to expand and push against the agent composition;

(3) quickly delivering the first beneficial agent from the compartment by the first beneficial agent formulation being dispensed in a beneficially effective amount through the first exit means by diffusion or erosion into the environment of use for a first period of time; and (4) delivering the second beneficial agent from the compartment by the expandable driving member continually expanding against the second beneficial agent formulation and causing the beneficial agent to be dispensed in a beneficially effective amount through the second exit means at a controlled rate to the environment of use over a prolonged period of time 11. A method according to claim 10 wherein the environment of use is the rumen of a ruminant animal and the dispenser further comprises a densifier.

12. A method according to claim 11 wherein the first beneficial agent and the second beneficial agent are the same beneficial agent.

13. A method according to claim 11 wherein the beneficial agent is an ionophore.

14. A method according to claim 12 wherein the beneficial agent is an ionophore.

15. A method according to claim 14 wherein the ionophore is lysocellin, lasalocid, tetronasin or laidlomycin propionate.

16. A method according to claim 10 wherein the diameter of each of the first exit passageways is 100 mil or larger, and the diameter of each of the second exit passageways is from about 60 mil to about 95 mil.

17. A method according to claim 16 wherein the environment of use is the rumen of a ruminant animal, the dispenser further comprises a densifier, and the beneficial agent is an ionophore.

18. A method according to claim 17 wherein the first beneficial agent and the second beneficial agent are the same ionophore, and the ionophore is chosen from lysocellin, lasalocid, tetronasin and laidlomycin propionate.

19. A delivery device according to claim 1 wherein the environment of use is the rumen of a ruminant animal and the delivery device further comprises a density element.

20. A delivery device according to claim 7 wherein the environment of use is the rumen of a ruminant animal, the delivery device further comprises a density element, and the beneficial agent is an ionophore.

21. A delivery device according to claim 20 wherein the first beneficial agent and the second beneficial agent are the same ionophore, and the ionophore is chosen from lysocellin, lasalocid, tetronasin and laidlomycin propionate.

* * * * *